(12) United States Patent
Connors et al.

(10) Patent No.: US 7,878,206 B2
(45) Date of Patent: Feb. 1, 2011

(54) SYSTEM AND METHOD FOR TREATMENT OF UVULA AND SOFT PALATE TO REDUCE TISSUE LAXITY

(75) Inventors: Kevin P. Connors, San Francisco, CA (US); David A. Gollnick, San Francisco, CA (US); Dean A. MacFarland, Magnolia, MA (US); Scott A. Davenport, Half Moon Bay, CA (US)

(73) Assignee: Cutera, Inc., Brisbane, CA (US)

( * ) Notice: Subject to any disclaimer, the term of this patent is extended or adjusted under 35 U.S.C. 154(b) by 212 days.

(21) Appl. No.: 12/349,295

(22) Filed: Jan. 6, 2009

(65) Prior Publication Data

US 2009/0131923 A1 May 21, 2009

Related U.S. Application Data

(63) Continuation of application No. 11/327,106, filed on Jan. 6, 2006, now abandoned.

(60) Provisional application No. 60/642,357, filed on Jan. 7, 2005.

(51) Int. Cl.
*A61B 19/00* (2006.01)
(52) U.S. Cl. .............................. 128/898; 606/2; 607/88
(58) Field of Classification Search ................ 128/898; 606/2, 27; 607/88, 89, 96, 100
See application file for complete search history.

(56) References Cited

U.S. PATENT DOCUMENTS

| 4,233,493 | A | 11/1980 | Nath | 219/354 |
|---|---|---|---|---|
| 5,735,844 | A | 4/1998 | Anderson et al. | 606/8 |
| 5,743,870 | A | 4/1998 | Edwards | 604/22 |
| 6,997,923 | B2 | 2/2006 | Anderson et al. | 606/9 |
| 7,090,670 | B2 | 8/2006 | Sink | 606/9 |
| 2003/0216719 | A1* | 11/2003 | Debenedictis et al. | 606/10 |
| 2005/0049582 | A1 | 3/2005 | DeBenedictis et al. | 606/9 |
| 2005/0171581 | A1 | 8/2005 | Connors et al. | 607/88 |

OTHER PUBLICATIONS

Beam Multiplication: Application Note, www.holoor.co.il/Website/data/publications/Appl_BM2.pdf, date pre-2005, one page in length.

Bryan W. Rubach, et al., "Histological and Clinical Evaluation of Facial Resurfacing Using a Carbon Dioxide Laser With the Computer Pattern Generator," *Archives of Otolaryngology-Head & Neck Surgery* (1997), vol. 123, No. 9, 6 pages in length.

* cited by examiner

*Primary Examiner*—Ahmed M Farah
(74) *Attorney, Agent, or Firm*—Morrison & Foerster LLP

(57) ABSTRACT

System and methods for minimally invasive treatment of snoring are described. According to one system and method, laser energy is applied to tissue of a soft palate and/or uvula to create a pattern of multiple treatment spots in the tissue. According to another system and method, electromagnetic energy from a filament light source is impinged of soft palate and/or uvula tissue to achieve volumetric heating of the tissue. The systems and methods increase rigidity and/or reduce laxity of the tissue, and/or volumetrically reduce the tissue, thereby diminishing snoring.

24 Claims, 6 Drawing Sheets

US 7,878,206 B2

SYSTEM AND METHOD FOR TREATMENT OF UVULA AND SOFT PALATE TO REDUCE TISSUE LAXITY

PRIORITY CLAIMS

This application is a continuation of U.S. application Ser. No. 11/327,106, filed Jan. 6, 2006 now abandoned, and claims priority to prior provisional application Ser. No. 60/642,357, filed Jan. 7, 2005, both of which are incorporated herein by reference.

FIELD OF THE INVENTION

This present invention relates to treatment of the uvula and soft palate, with the purpose of reducing the amount of tissue laxity, to reduce snoring.

BACKGROUND OF THE INVENTION

In the past a number of different procedures have been used to attempt to reduce snoring by reducing the laxity of the tissue in the soft palate and uvula areas. These procedures include surgical methods such as uvulopalatopharyngoplasty (UPPP) with cold steel, RF uvulopalatopharyngolasty using radio frequency, laser assisted uvula platoplasty (LUPP), using relatively extensive laser incisions, injection snoreplasty with a sclerotherapy agent and laser soft palate stiffening with implantable woven inserts. U.S. Pat. No. 5,743,870 describes systems for ablating and removing uvula and soft palate tissue for reducing snoring.

Embodiments of the system and method described herein provide for different anti-snoring treatments which are minimally-invasive, have low intervention risk, can be performed in an office setting, and provide for significantly decreased morbidity.

DESCRIPTION OF THE INVENTION

Figure 1:
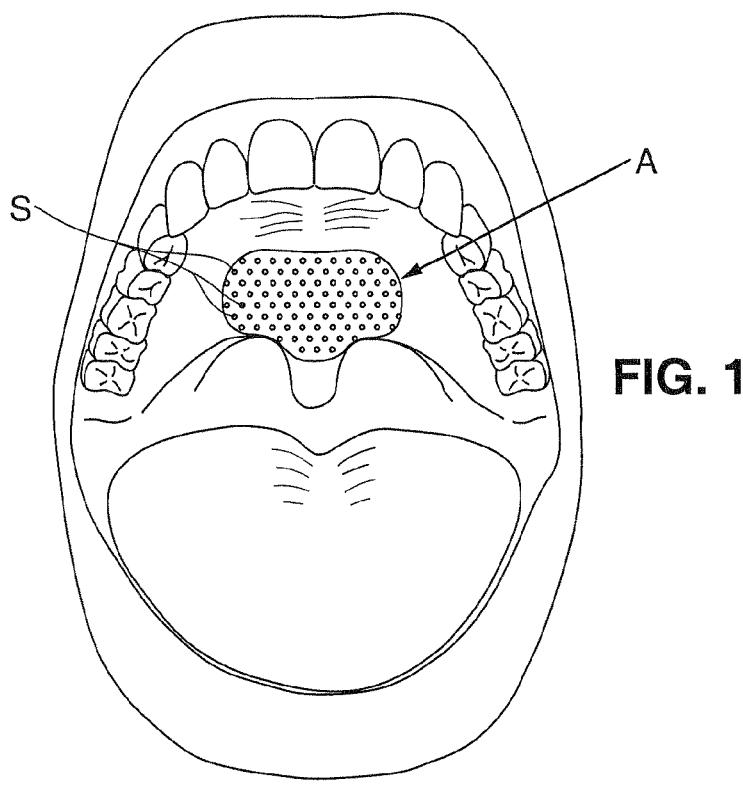
FIG. 1 is an illustration of a patient's open mouth, illustrating a multispot treatment area covering portions of the soft palate and uvula.
Figure 2:
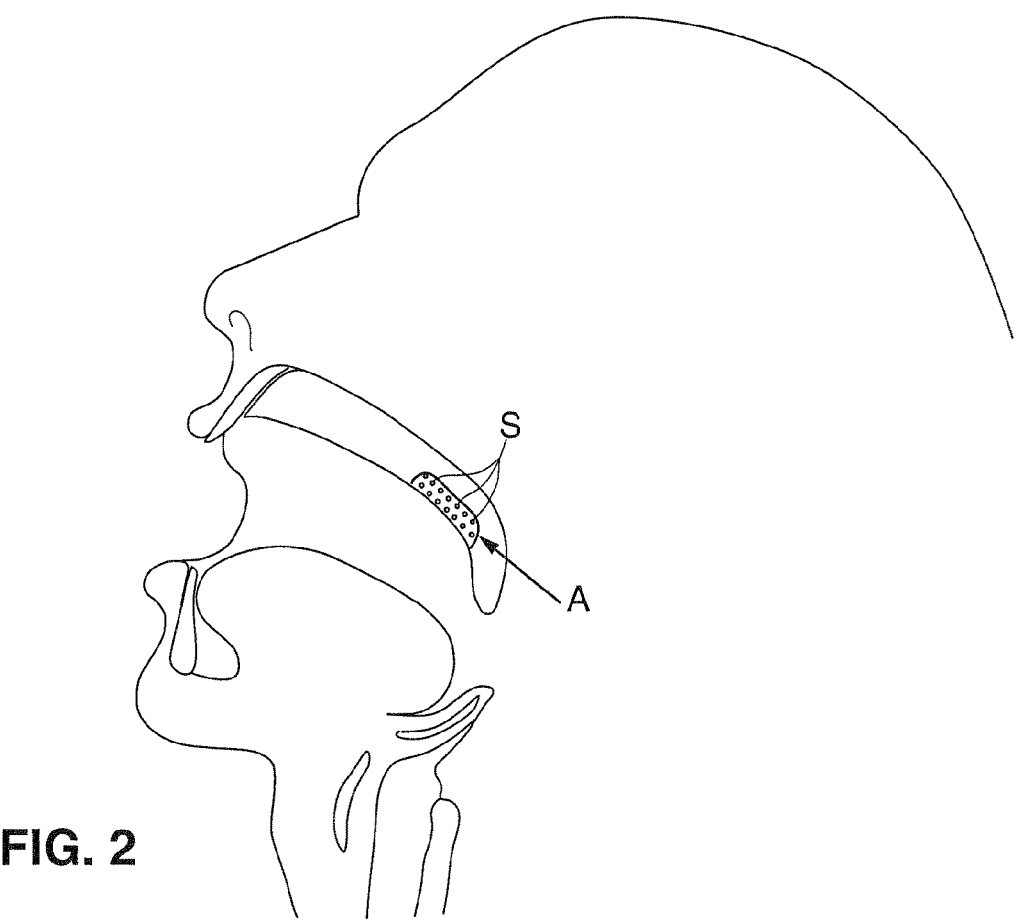
FIG. 2 is schematic side view of a patient's head and open mouth, further illustrating the multispot treatment area shown in FIG. 1.

FIGS. 1 and 2 are illustrations of a patient's open mouth, in which area A generally corresponds to an area of the uvula and the soft palate area. Snoring can result from lax or redundant tissue in the tissue of the soft palate and uvula, and in many cases snoring can be reduced or eliminated by reducing the laxity of the tissue in these areas. Embodiments herein provide for safe and non-invasive, or relatively non-invasive, systems and methods for creating thermal damage to the soft plate and/or uvula. Depending on the parameters of the applied energy, the thermal damage can reduce snoring in one or more of a variety of ways. For example, in some embodiments the thermal damage diminishes snoring by inducing fibrosis in the thermally damaged tissue, thus reducing the laxity of the tissue in these areas. In other methods, the thermal damage causes tissue necrosis. Over time the necrosed tissue is absorbed by the body, thus reducing the volume of the area treated. Still other methods use high intensity energy to vaporize tissue, thus volumetrically reducing the tissue.

The disclosed embodiments employ systems and methods for applying electromagnetic energy (including, but not limited to, laser energy or electromagnetic energy in the infrared and/or near-infrared range of the electromagnetic spectrum) to the tissue of the soft palate and/or uvula (or other tissues associated with snoring, such as the nasal turbinates) in order to promote rigidity or stiffness of the tissue, or to volumetrically reduce the tissue.

According to a first exemplary method, laser energy is used to produce a pattern of 10 um to 1 mm thermally damaged or ablated spots ("treatment spots") in soft palate and/or uvula tissues. FIG. 1 illustrates an example of multiple spots S formed by laser energy applied to area A of tissue. The regions of tissue surrounding and between the spots S include viable tissue.

The spots S may be formed simultaneously or sequentially. Tissue damage within these spots preferably extends to a depth of 0.1 mm to 5 mm. The laser wavelength, fluence and pulse characteristics are chosen to be haemostatic so bleeding is either not present or minimized. Many wavelengths are suitable for the procedure, including but not limited to 532 nm, 910 nm, 1064 nm, 1540 nm, and 2100 nm. The small dimension of the individual spots allows relatively quick healing of the mucosal and sub mucosal tissues. The pattern density can be varied to optimize the results. The ratio of treated to untreated area within a treatment area is preferably less than 50% and most preferably less than 20%. One example of a treatment method of this type uses the following specifications:

wavelength 532 nm
spot size 0.5 mm
pattern density 10%
pulse width 3 ms
fluence 30 J/cm^2.

Modifications to the first embodiment may be made so as to thermally damage the sub mucosa while preventing or minimizing damage to the mucosa. A modification of this type might include clamping or cooling of the mucosal layer while the laser energy is being deposited. This would result in the damage occurring primarily or exclusively in the sub mucosa. As one example, cooling might be achieved by passing the laser energy through a cooled sapphire window using a cooling system of the type described below in connection with FIG. 7.

According to the first exemplary method, the lax soft palate tissue increases in rigidity or stiffness upon treatment due to both collagen heating peripheral to the spots and stiffening or volumetric reduction due to healing of thermally damaged spots and or ablation of tissue within the spots.

Figure 3:
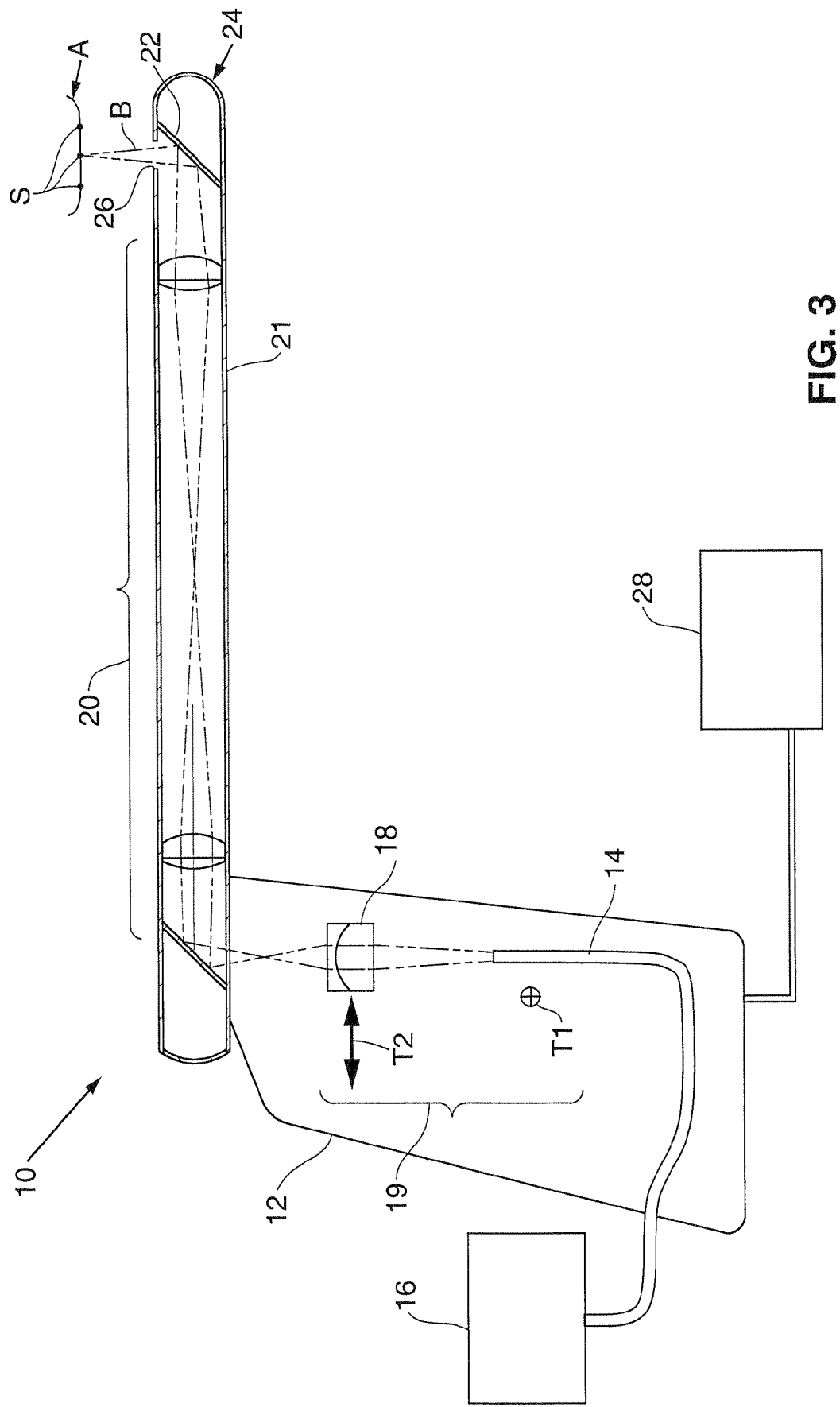
FIGS. 3 and 4 illustrate first and second embodiments, respectively, of systems useful for creating treatment spots.
Figure 4:
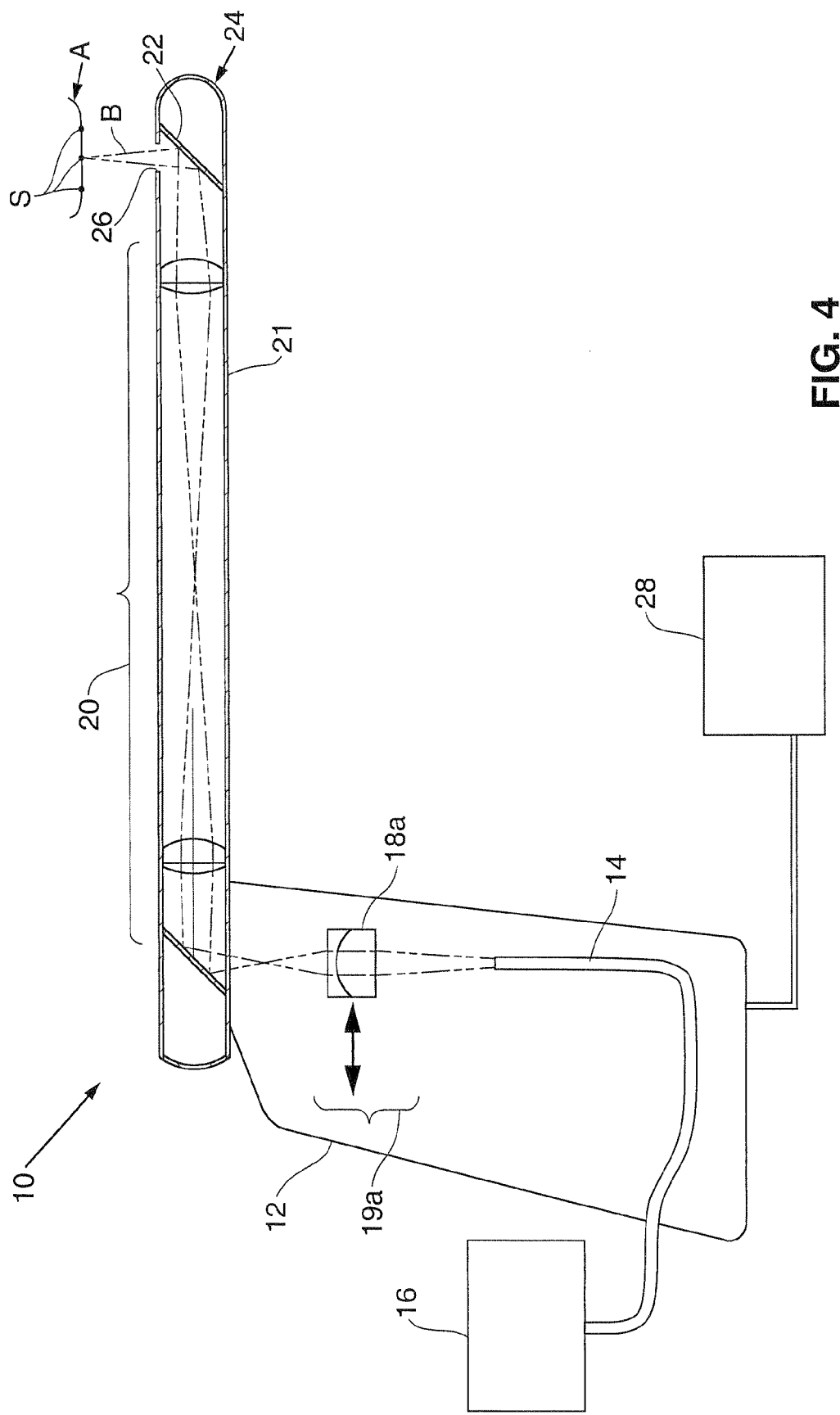

FIGS. 3 and 4 illustrate systems useful in creating multiple treatment spots. These systems use scanner technology to sequentially move a beam of laser light from one tissue spot to the next to create a pre-determined pattern of treated tissue spots.

Referring to FIG. 3, system 10 includes handpiece 12 designed to provide for the delivery of laser light through an optical fiber 14 and an associated optical system to a treatment site. Optical fiber 14 is coupled to a laser light source 16.

A lens 18 forms an image of the optical fiber. A scanning system 19 allows for movement of the image in two-dimensions. In this embodiment, translation of the optical fiber 14 in the direction illustrated by T1 (perpendicular to the plane of the page) will move the image linearly in a first direction, and translation of the lens 16 as illustrated by arrow T2 will move the image linearly in a second direction orthogonal to the first direction. Although the FIG. 3 embodiments use two linear stepper motors to translate the optical fiber and the lens, other suitable devices include stepper motors, voice coil actuators and/or galvanometer scanners.

Handpiece 12 includes an elongate cannula 21. An optical relay system 20 within the cannula couples the laser energy to the tissue. A mirror 22 at the distal end 24 of the cannula 21 deflects the beam through a window 26 to tissue in the desired tissue area A.

One or more control systems 28 control operation of the scanning system 19, the laser light source 16, and/or other systems associated with the device (e.g. a cooling system).

To use the system 10, the distal end 24 is positioned in a patient's mouth, with the window 26 oriented towards the target tissue area A. Delivery of laser energy is activated such as by depressing a button on handpiece 12 or through activation of a footswitch. During treatment, the scanning system sequentially directs a beam B of laser energy to each of a plurality of spots. One or more or pulses of energy are delivered to each spot, thus producing a pattern of treated spots within the treatment area. In a preferred method, the path of beam B is repositioned during intervals where laser energy is briefly suspended or between pulses to allow a discrete array of treatment spots to be formed.

FIG. 4 provides a modified embodiment where the optical fiber is fixed and the lens 18a is scanned in two axes with either two stepper motors or voice coils. The treatment spot is relay imaged as in the embodiment of FIG. 3.

The scanning system is preferably programmed to direct the path of the beam to each of a plurality of predetermined treatment spots. However in an alternative system the handpiece might include actuators allowing the user to selectively prompt the scanning system to re-direct the path of the energy beam in a direction along one or both of the scanner's axes, thus allowing for energy delivery to a spot of the users choosing. A simplified embodiment might be provided without a scanning system, thus requiring the user to re-position the path of the energy beam by manually re-positioning the handpiece.

Figure 5:
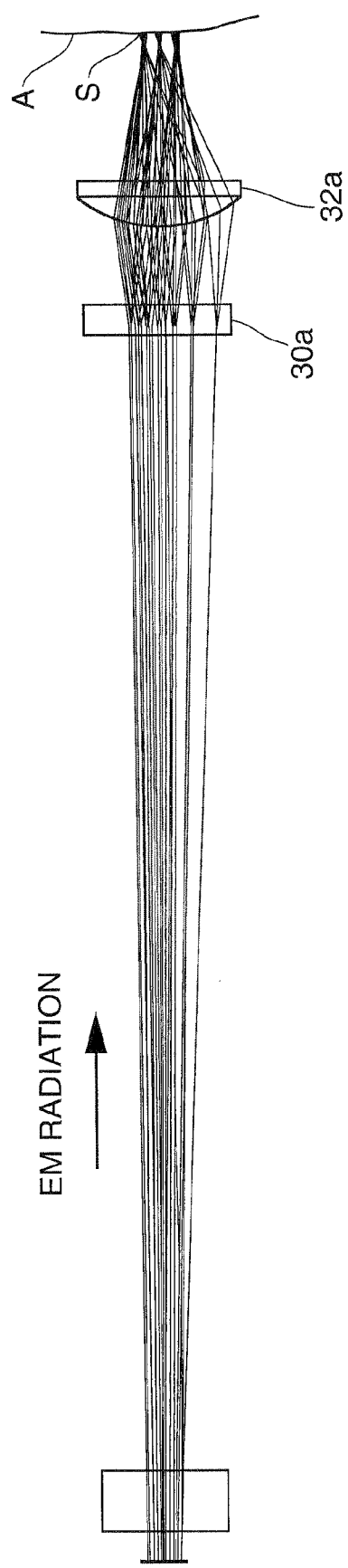
FIGS. 5 and 6 schematically illustrate the use of beam splitting devices to create patterns of treatment spots.
Figure 6:
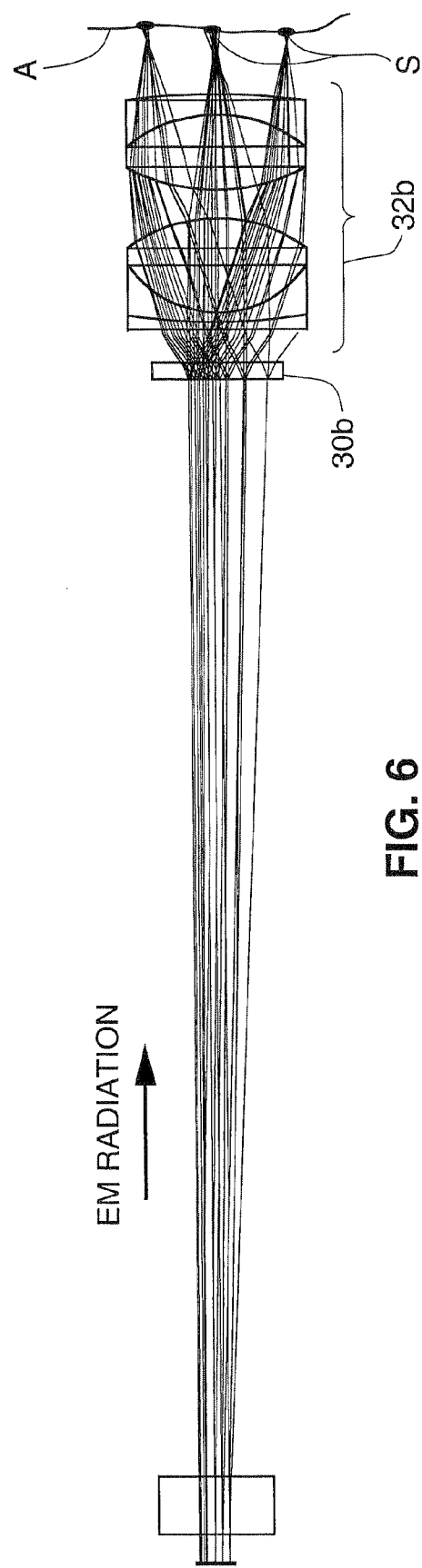

FIGS. 5-6 illustrate aspects of an embodiment which utilizes beam multiplexing, where a beam splitting device 30a (FIG. 5) or 30b (FIG. 6) is used to create a pattern of spots. Using the FIGS. 5 and 6 embodiments, laser energy may be simultaneously applied to the multiple treatment spots in the tissue. A single lenses 32a or a lens system 32b may be employed as needed to focus the multiplexed beam into a desired pattern of foci.

In the FIGS. 5 and 6 embodiments, the beam-splitting devices 28a, 28b may be diffractive elements, such as a Dammann type of diffractive phase grating, where the diffractive orders have equal intensity. FIGS. 5-6 show a diffraction element, which could be for example a grating of fused silica and optical ray traces of the electromagnetic radiation are shown. On-line publication entitled BEAM MULTIPLICATION: Application Note, www.holoor.co.il/Website/data/publications/Appl_BM2.pdf, illustrates known diffractive elements and their use for beam multiplexing, and lists other prior technical publications on this technology.

Alternate systems and methods allowing for sequential or simultaneous delivery of optical energy to multiple skin locations are described in U.S. Publication No. 2005/0049582 A1, entitled METHOD AND APPARATUS FOR FRACTIONAL PHOTOTHERAPY OF SKIN. Although not concerned with treatment of tissue of the soft palate or uvula, certain systems, parameters and methods disclosed in that application might be beneficially employed in conjunction with the systems and methods disclosed in the present application.

A second exemplary method heats a volume of tissue using infrared or near infrared electromagnetic (EM) radiation over a relatively large area to produce volumetric heating for a controlled amount of time in soft palate tissues. The thermal profile created by the device is an inverted thermal gradient, with the surface mucosal temperature lower than deeper sub mucosal tissue temperature. An inverted thermal gradient provides a continuous variation in temperature as a function of tissue depth, in which the superficial mucosal layers are at lower temperatures than the deeper tissues. The surface mucosal temperature is held to a safe level while the deeper sub mucosal tissue is heated by the EM radiation. US Publication No. 2005-0171581, entitled SYSTEM AND METHOD FOR HEATING SKIN USING LIGHT TO PROVIDE TISSUE TREATMENT, which is assigned to the same assignee as this present provisional application, provides a number details regarding the operation of a near infra-red (NIR) energy source to provide an inverted thermal gradient in tissue. Many of the principals discussed in the prior application are applicable to the treatment discussed in this present application.

Optimal heating is produced through control of the absorption depth profile associated with the penetration of the applied EM radiation to the tissues. The temperature profile and its duration affect the lax tissue in such a way as to induce rigidity or stiffness of the tissue. Desired depth profiles produce significant temperature rises between 1 and 5 millimeters.

Figure 7:
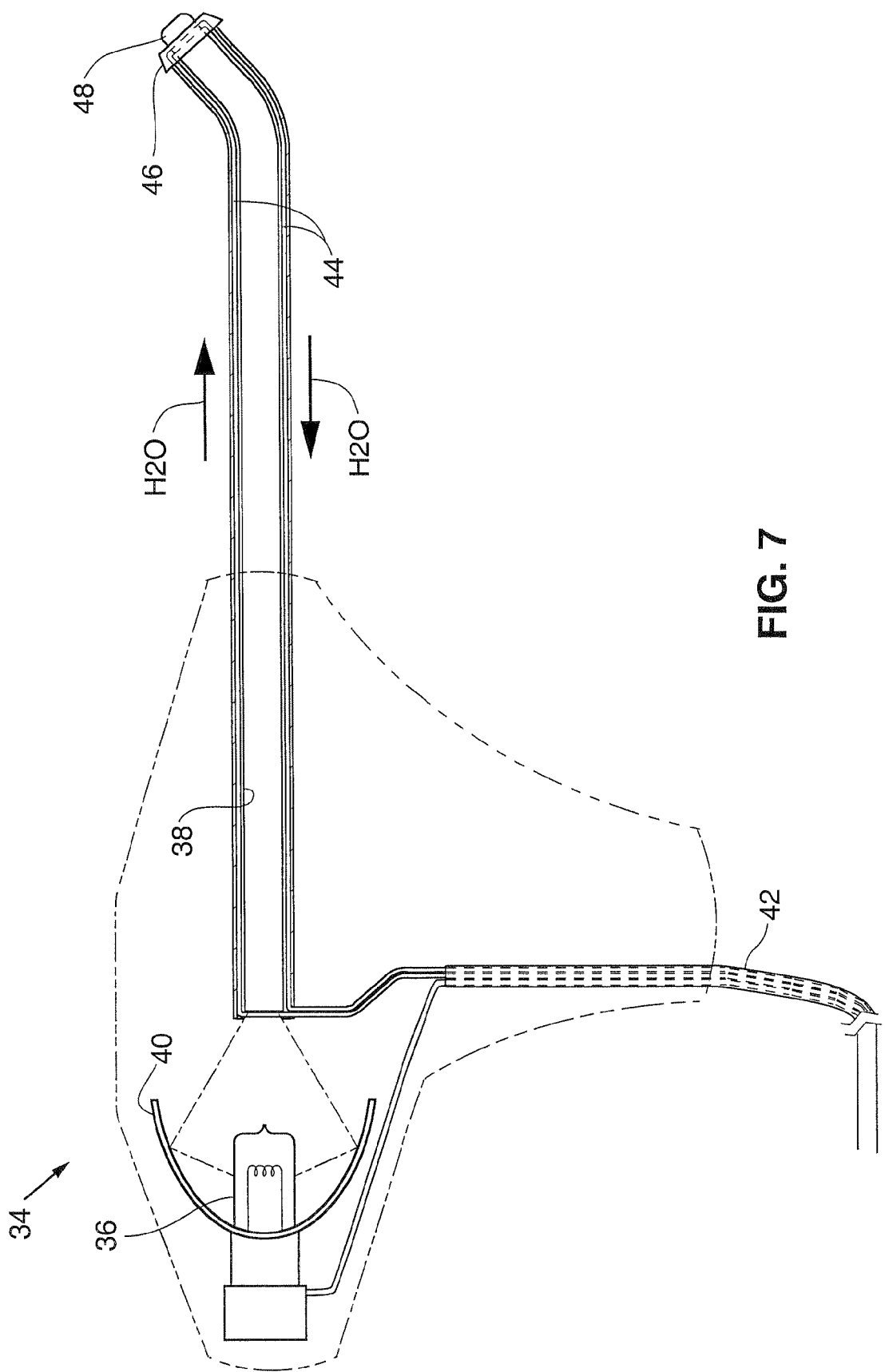
FIG. 7 illustrates a third embodiment of a system useful for creating treatment spots.

FIG. 7 shows an embodiment of an infrared volumetric heating system 34 useful for practicing the second exemplary method. Specifically, FIG. 7 shows a tungsten-halogen filament lamp 36 coupled into an infrared light guide 38 with a gold parabolic reflector 40. Cold water is circulated via thin tubing 42 and water lines 44 between a water source (not shown) and a copper jacket 46, thereby cooling the copper jacket 46. A sapphire window 48 is mounted to the copper jacket 46 and the infrared light guide 38. The window 48 is chilled by the copper jacket 46 and transmits IR light through it. The temperature regulated sapphire window 48 is placed in contact with the soft palate mucosa. This both transmits the IR radiation into the tissue and clamps the surface tissue temperature. Aspects of a system for coupling EM radiation into a fiber for providing treatment to tissue are discussed in U.S. Pat. No. 4,233,493, and elements from the teaching of the '493 patent could be included in an embodiment of the system and method of this present provisional application.

While various embodiments of the present invention have been described above, it should be understood that they have been presented by way of example, and not limitation. It will be apparent to persons skilled in the relevant art that various changes in form and detail may be made therein without departing from the spirit and scope of the invention. This is especially true in light of technology and terms within the relevant art(s) that may be later developed. Thus, the present invention should not be limited by any of the above-described exemplary embodiments, but should be defined only in accordance with the following claims and their equivalents.

Any and all patents, patent applications and printed publications referred to above are incorporated by reference.

What is claimed is:

1. A method for treatment of snoring, comprising:
 inserting an elongate cannula having a longitudinal axis into a mouth of a patient; and applying optical energy to tissue of a soft palate and/or uvula to create a pattern of multiple treatment spots in the tissue, said optical energy passing from the cannula towards the tissue in a direction transverse to and away from the longitudinal axis of the cannula.

2. The method according to claim 1, wherein the treatment spots are discrete zones of thermally damaged tissue.

3. The method according to claim 2, wherein the pattern includes regions of healthy tissue interspersed between the treatment spots.

4. The method according to claim 1, wherein the applying step includes sequentially impinging laser energy onto each of plurality of tissue locations to create the pattern.

5. The method according to claim 4, wherein the method includes the step of providing an optical system for directing laser energy onto tissue and a scanning system operable to reposition elements of the optical system, and wherein the step of sequentially impinging laser energy includes the step of causing the scanning system to sequentially reposition elements of the optical system.

6. The method according to claim 5, wherein the providing step further provides a handpiece including the optical system and the scanning system, and wherein the repositioning step is performed without repositioning the handpiece.

7. The method according to claim 1, wherein the applying step includes simultaneously directing multiple beams of laser energy onto the tissue to create the pattern.

8. The method of claim 7, wherein the applying step includes passing laser light through a diffractive element.

9. The method according to claim 1, wherein the treatment spots have a cross-sectional width in the range of approximately 10 um to 1 mm.

10. The method according to claim 1, wherein the treatment spots extend to a depth within the range of 0.1 mm to 5 mm.

11. The method according to claim 1, wherein the treatment spots lie within a treatment area bounded by treatment spots, and wherein the ratio of treated to untreated area within the treatment area is less than 50%.

12. The method according to claim 11, wherein the ratio is less than 20%.

13. The method according to claim 1, wherein the method increases rigidity and/or reduces laxity of the tissue.

14. The method according to claim 1, further including the step of cooling a surface of the tissue.

15. The method according to claim 14, wherein the cooling step includes positioning a cooled window in contact with the tissue, and applying the optical energy through the window.

16. The method according to claim 1, wherein the cannula includes an elongate portion having the longitudinal portion, and an angular distal portion, and wherein during the step of applying the optical energy, the optical energy passes from the angular distal portion of the cannula towards the tissue.

17. The method according to claim 1, wherein the cannula includes a tubular sidewall having a window, and wherein during the step of applying the optical energy, the optical energy passes from the window of the cannula towards the tissue.

18. A method for treatment of snoring, comprising:
inserting an elongate cannula having a longitudinal axis into a mouth of a patient; and
applying electromagnetic radiation from a filament light source onto tissue of a soft palate and/or uvula, said electromagnetic radiation energy passing from the cannula towards the tissue in a direction transverse to and away from the longitudinal axis of the cannula.

19. The method of claim 18, wherein the electromagnetic radiation includes infrared and/or near infrared electromagnetic radiation.

20. The method of claim 18, wherein the tissue includes sub mucosal tissue and surface mucosa, and wherein the electromagnetic radiation heats the sub mucosal tissue to a temperature higher than a temperature of corresponding surface mucosa.

21. The method according to claim 18, further including the step of cooling a surface of the tissue.

22. The method of claim 21, wherein the cooling step includes positioning a cooled window in contact with the tissue, and passing the electromagnetic radiation through the window.

23. The method of claim 18, wherein the electromagnetic radiation is emitted by a tungsten-halogen lamp.

24. The method according to claim 18, wherein the method increases rigidity and/or reduces laxity of the tissue.

* * * * *